United States Patent [19]

Lowe, III et al.

[11] Patent Number: 5,744,480

[45] Date of Patent: Apr. 28, 1998

[54] FLUOROALKOXYBENZYLAMINO DERIVATIVES OF NITROGEN CONTAINING HETEROCYCLES

[75] Inventors: John Adams Lowe, III, Stonington, Conn.; Terry Jay Rosen, Foster City, Calif.

[73] Assignee: Pfizer Inc., New York, N.Y.

[21] Appl. No.: 443,418

[22] Filed: May 22, 1995

Related U.S. Application Data

[60] Division of Ser. No. 167,881, Dec. 14, 1993, which is a continuation-in-part of Ser. No. 717,943, Jun. 20, 1991.

[51] Int. Cl.$^6$ .................... C07D 453/02; A61K 31/44
[52] U.S. Cl. ............................... 514/305; 546/133
[58] Field of Search ........................ 546/133; 514/305

[56] References Cited

U.S. PATENT DOCUMENTS 3,560,510  2/1971  Warawa .................. 546/133

5,138,060  8/1992  Godek et al. .................. 546/133

Primary Examiner—Alan L. Rotman
Attorney, Agent, or Firm—Peter C. Richardson; Paul H. Ginsburg; Karen DeBenedictis

[57] ABSTRACT

The present invention relates to novel fluoroalkoxybenzylamino derivatives of nitrogen containing heterocyclic compounds, and specifically, to compounds of the formula

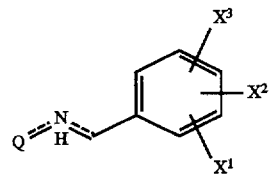

wherein Q, $X^1$, $X^2$ and $X^3$ are as defined below. These novel compounds are useful in the treatment of inflammatory and central nervous system disorders, as well as other disorders.

20 Claims, No Drawings

FLUOROALKOXYBENZYLAMINO DERIVATIVES OF NITROGEN CONTAINING HETEROCYCLES

This is a division of application Ser. No. 08/167,881, filed on Dec. 14, 1993 which is a continuation-in-part of U.S. Ser. No. 717,943, which was filed on Jun. 20, 1991.

BACKGROUND OF THE INVENTION

The present invention relates to novel fluoroalkoxybenzylamino derivatives of nitrogen containing heterocycles, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P receptor antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

In the recent past, some attempts have been made to provide antagonists for substance P and other tachykinin peptides in order to more effectively treat the various disorders and diseases listed above. The few such antagonists thus far described are generally peptide-like in nature and are therefore too labile from a metabolic point of view to serve as practical therapeutic agents in the treatment of disease. The non-peptidic antagonists of the present invention, on the other hand, do not possess this drawback, being far more stable from a metabolic point of view than the agents referred to above.

Quinuclidine derivatives and related compounds that exhibit activity as substance P receptor antagonists are referred to in PCT Patent Application PCT/US 89/05338, filed Nov. 20, 1989 and U.S. patent application Ser. No. 557,442, filed Jul. 23, 1990, both of which are assigned in common with the present application. Similar compounds are referred to in PCT patent applications PCT/US 91/02853 and PCT/US 91/03369, filed on Apr. 25, 1991 and May 15, 1991, respectively. These applications are also assigned in common with the present application.

Piperidine derivatives and related heterocyclic nitrogen containing compounds that are useful as substance P antagonists are referred to in U.S. patent application Ser. No. 619,361, filed Nov. 28, 1990 and U.S. patent application Ser. No. 590,423, filed Sep. 28, 1990, both of which are assigned in common with the present application.

SUMMARY OF THE INVENTION

The present invention relates to compounds of the formula

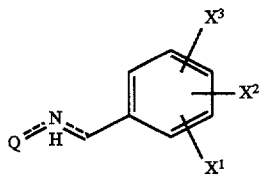

wherein $X^1$ is hydrogen, $(C_1-C_{10})$ alkoxy optionally substituted with from one to three flourine atoms or $(C_1-C_{10})$ alkyl optionally substituted with from one to three fluorine atoms;

$X^2$ and $X^3$ are independently selected from hydrogen, halo, nitro, $(C_1-C_{10})$ alkyl optionally substituted with from one to three fluorine atoms, $(C_1-C_{10})$ alkoxy optionally substituted with from one to three fluorine atoms, trifluoromethyl, hydroxy, phenyl, cyano, amino, $(C_1-C_6)$-alkylamino, di-$(C_1-C_6)$alkylamino, $$-\overset{O}{\underset{\|}{C}}-NH-(C_1-C_6)\text{alkyl}, (C_1-C_6)\text{ alkyl-}\overset{O}{\underset{\|}{C}}-NH-(C_1-C_6)\text{ alkyl},$$

hydroxy$(C_1-C_4)$alkyl, $(C_1-C_4)$alkoxy$(C_1-C_4)$alkyl, $$-\overset{O}{\underset{\|}{NHCH}} \text{ and } -\overset{O}{\underset{\|}{NHC}}-(C_1-C_6) \text{ alkyl};$$

and

Q is a group of the formula

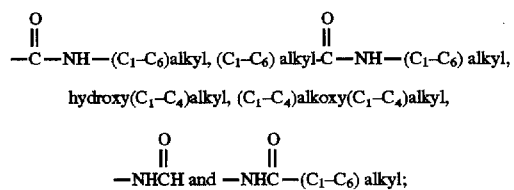

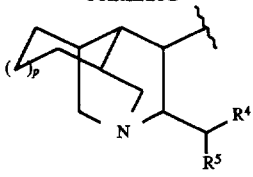

VI

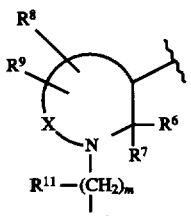

VII

OR

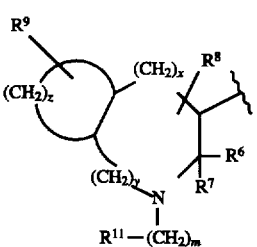

VIII wherein

R¹ is a radical selected from furyl, thienyl, pyridyl, indolyl, biphenyl and phenyl optionally substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, benzyloxycarbonyl and $(C_1-C_3)$ alkoxy-carbonyl;

R¹³ is selected from $(C_3-C_4)$ branched alkyl, $(C_5-C_6)$ branched alkenyl, $(C_5-C_7)$ cycloalkyl, and the radicals named in the definition of R¹;

R² is hydrogen or $(C_1-C_6)$ alkyl;

R³ is phenyl, biphenyl, naphthyl, pyridyl, benzhydryl, thienyl or furyl, and R³ may optionally be substituted with from one to three substituents independently selected from halo, $(C_1-C_{10})$ alkyl optionally substituted with from one to three fluorine atoms and $(C_1-C_{10})$ alkoxy optionally substituted with from one to three fluorine atoms;

Y is $(CH_2)_l$ wherein l is an integer from one to three, or Y is a group of the formula

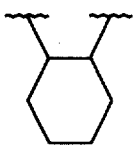

(J)

Z is oxygen, sulfur, amino, $(C_1-C_3)$alkylamino or $(CH_2)_n$ wherein n is zero, one or two;

o is two or three;

p is zero or one;

R⁴ is furyl, thienyl, pyridyl, indolyl, biphenyl, or phenyl optionally substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, $(C_1-C_3)$ alkoxy-carbonyl and benzyloxycarbonyl;

R⁵ is thienyl, biphenyl or phenyl optionally substituted with one or two substituents independently selected from halo, $(C_1-C_{10})$ alkyl optionally substituted with from one to three fluorine atoms and $(C_1-C_{10})$ alkoxy optionally substituted with from one to three fluorine atoms;

each of the two dashed lines in formula I and the dashed line in formula II represent an optional double bond that may optionally exist when Q is a group of the formula II;

X is $(CH_2)_q$ wherein q is an integer from 1 to 6, and wherein any one of the carbon—carbon single bonds in said $(CH_2)_q$ may optionally be replaced by a carbon—carbon double bond, and wherein any one of the carbon atoms of said $(CH_2)_q$ may optionally be substituted with R⁸, and wherein any one of the carbon atoms of said $(CH_2)_q$ may optionally be substituted with R⁹;

m is an integer from 0 to 8, and any one of the carbon—carbon single bonds of $(CH_2)_m$ may optionally be replaced by a carbon—carbon double bond or a carbon—carbon triple bond, and any one of the carbon atoms of said $(CH_2)_m$ may optionally be substituted with R¹¹;

R⁶ is a radical selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents independently selected from halo, nitro, $(C_1-C_{10})$ alkyl optionally substituted with from one to three fluorine atoms, $(C_1-C_{10})$ alkoxy optionally substituted with from one to three fluorine atoms, amino, hydroxy-$(C_1-C_6)$alkyl, $(C_1-C_6)$alkoxy-$(C_1-C_6)$alkyl,

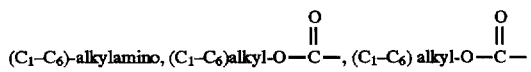

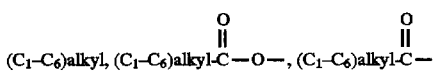

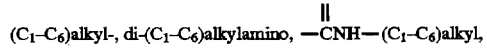

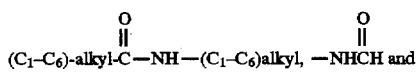

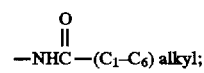

and wherein one of the phenyl moieties of said benzhydryl may optionally be replaced by naphthyl, thienyl, furyl or pyridyl;

R⁷ is hydrogen, phenyl or $(C_1-C_6)$alkyl;

or R⁶ and R⁷, together with the carbon to which they are attached, form a saturated carbocyclic ring having from 3 to 7 carbon atoms wherein one of said carbon atoms may optionally be replaced by oxygen, nitrogen or sulfur;

R⁸ and R⁹ are each independently selected from hydrogen, hydroxy, halo, amino, oxo (=O), nitrile, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino, $(C_1-C_6)$alkoxy,

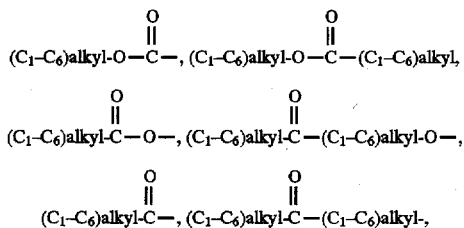

and the radicals set forth in the definition of $R^6$;

$R^{10}$ is $NHCR^{12}$, $NHCH_2R^{12}$, $NHSO_2R^{12}$ or one of the radicals set forth in any of the definitions of $R^6$, $R^8$ and $R^9$;

$R^{11}$ is oximino (=NOH) or one of the radicals set forth in any of the definitions of $R^6$, $R^8$ and $R^9$; and $R^{12}$ is $(C_1-C_6)$alkyl, hydrogen, phenyl$(C_1-C_6)$alkyl or phenyl optionally substituted with $(C_1-C_6)$ alkyl; and with the proviso that (a) when m is 0, $R^{11}$ is absent, (b) neither $R^8$, $R^9$, $R^{10}$ nor $R^{11}$ can form, together with the carbon to which it is attached, a ring with $R^7$, (c) when Q is a group of the formula VIII, $R^8$ and $R^9$ cannot be attached to the same carbon atom, (d) when $R^8$ and $R^9$ are attached to the same carbon atom, then either each of $R^8$ and $R^9$ is independently selected from hydrogen, fluoro, $(C_1-C_6)$ alkyl, hydroxy-$(C_1-C_6)$alkyl and $(C_1-C_6)$alkoxy-$(C_1-C_6)$alkyl, or $R^8$ and $R^9$, together with the carbon to which they are attached, form a $(C_3-C_6)$ saturated carbocyclic ring that forms a spiro compound with the nitrogen-containing ring to which they are attached, (e) the nitrogen of formula I can not be double bonded to both Q and the substituted benzyl group to which it is attached, (f) when Q is a group of the formula VII and q is 2 and either $R^8$ or $R^9$ is 5-hydroxy-$(C_1-C_6)$alkyl or 5-$(C_1-C_6)$alkoxy-$(C_1-C_6)$ alkyl, then the other of $R^8$ and $R^9$ is either 5-$(C_1-C_3)$ alkyl or hydrogen; (g) when Q is a group of the formula VII and q is 2, then neither $R^8$ nor $R^9$ is 4-hydroxy-$(C_1-C_6)$alkyl or 4-$(C_1-C_6)$alkoxy-$(C_1-C_6)$alkyl, and (h) when neither $X^1$, $X^2$ nor $X^3$ is a fluorinated alkoxy group, at least one of $R^1$, $R^3$, $R^4$, $R^5$, $R^6$, $R^7$ and $R^{13}$ is an aryl group substituted with a fluorinated alkoxy group.

The present invention also relates to the pharmaceutically acceptable acid addition and base salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

Preferred compounds of the formula I are those wherein $R^1$, $R^4$, $R^5$ and $R^7$ are phenyl, $R^2$ is hydrogen, $R^3$ is phenyl optionally substituted with chlorine, fluorine, $(C_1-C_6)$ alkyl optionally substituted with from one to three fluorine atoms or $(C_1-C_6)$ alkoxy optionally substituted with from one to three fluorine atoms, m is 0 and n is 3 or 4.

Specific preferred compounds of the formula I are:

(2S,3S)-3-(5-tert-butyl-2-methoxybenzyl)amino-2-(3-trifluoromethoxyphenyl)piperidine;
(2S,3S)-3-(2-isopropoxy-5-trifluoromethoxybenzyl)amino-2-phenyl-piperidine;
(2S,3S)-3-(2-ethoxy-5-trifluoromethoxybenzyl)amino-2-phenyl-piperidine;
(2S,3S)-3-(2-methoxy-5-trifluoromethoxybenzyl)-amino-2-phenylpiperidine;
(2S,3S)-3(-5-tert-butyl-2-trifluoromethoxybenzyl)amino-2-phenylpiperidine;
2-(diphenylmethyl)-N-(2-methoxy-5-trifluoromethoxyphenyl)methyl-1-azabicyclo[2.2.2]octan-3-amine;
(2S,3S)-3-[5-chloro-2-(2,2,2-trifluoroethoxy)benzyl]amino-2-phenylpiperidine;
(2S,3S)-3-(5-tert-butyl-2-trifluoromethoxybenzyl)amino-2-phenylpiperidine;
(2S,3S)-3-(2-isopropoxy-5-trifluoromethoxybenzyl)amino-2-phenylpiperidine;
(2S,3S)-3-(2-difluoromethoxy-5-trifluoromethoxybenzyl)amino-2-phenylpiperidine;
(2S,3S)-2-phenyl-3-[2-(2,2,2-trifluoroethoxybenzyl)aminopiperidine; and
(2S,3S)-2-phenyl-3-(2-trifluoromethoxybenzyl)]aminopiperidine.

Other compounds of the formula I are:

3-[N-(2-methoxy-5-trifluoromethoxybenzyl)-amino]-5,5-dimethyl-2-phenylpyrrolidine;
3-[N-(2-methoxy-5-trifluoromethoxy-benzyl)amino]-4,5-dimethyl-2-phenylpyrrolidine;
3-(2-cyclopropyloxy-5-trifluoromethoxybenzyl)amino-2-phenylpiperidine;
3-(2-cyclopropylmethoxy-5-trifluoromethoxybenzyl)amino-2-phenylpiperidine;
3-(2-difluoromethoxy-5-phenylbenzyl)amino-2-phenylpiperidine;
3-(5-cyclopropylmethoxy-2-difluoromethoxybenzyl)amino-2-phenylpiperidine;
3-(2-methoxybenzyl)amino-2-(3-trifluoromethoxyphenyl)piperidine;
3-(2-methoxy-5-trifluoromethoxybenzyl)amino-2-(3-trifluoromethoxyphenyl)piperidine;
2-phenyl-3-(5-n-propyl-2-trifluoromethoxybenzyl)aminopiperidine;
3-(5-isopropyl-2-trifluoromethoxybenzyl)amino-2-phenylpiperidine;
3-(5-ethyl-2-trifluoromethoxybenzyl)amino-2-phenylpiperidine;
3-(5-sec-butyl-2-trifluoromethoxybenzyl)amino-2-phenylpiperidine;
3-(5-difluoromethoxy-2-methoxybenzyl)amino-2-phenylpiperidine;
3-(2-methoxy-5-trifluoromethoxybenzyl)amino-2-phenylpyrrolidine;
3-(2-methoxy-5-trifluoromethoxybenzyl)amino-2-phenylhomopiperidine;

2-benzhydryl-3-(2-methoxy-5-trifluoromethoxybenzyl) aminopyrrolidine;

2-benzhydryl-3-(2-methoxy-5-trifluoromethoxybenzyl) aminohomopiperidine;

3-[2,5-bis-(2,2,2-trifluoroethoxy)benzyl]amino-2-phenylpiperidine;

2-phenyl-3-(3-trifluoromethoxybenzyl)aminopiperidine;

2-benzhydryl-3-(2-methoxy-5-trifluoromethoxybenzyl) aminopiperidine;

1-(5,6-difluorohexyl)-3-(2-methoxy-5-trifluoromethoxybenzyl)amino-2-phenylpiperidine;

1-(6-hydroxyhexyl)-3-(2-methoxy-5-trifluoromethoxybenzyl)amino-2-phenylpiperidine;

3-phenyl-4-(2-methoxy-5-trifluoromethoxybenzyl)amino-2-azabicyclo[3.3.0]octane;

4-benzhydryl-5-(2-methoxy-5-trifluoromethoxybenzyl) amino-3-azabicyclo[4.1.0]heptane;

4-(2-methoxy-5-trifluoromethoxybenzyl)amino-3-phenyl-2-azabicyclo[4.4.0]decane;

2-phenyl-3-(2-methoxy-5-trifluoromethoxybenzyl) aminoquinuclidine;

8-benzhydryl-N-(2-methoxy-5-trifluoromethoxybenzyl)-9-azatricyclo[4.3.1.0$^{4,9}$]decan-7-amine;

9-benzhydryl-N-(2-methoxy-5-trifluoromethoxybenzyl)-10-azatricyclo[4.4.1.0$^{5,10}$]undecan-8-amine;

9-benzhydryl-N-(2-methoxy-5-trifluoromethoxybenzyl)-3-thia-10-azatricyclo[4.4.1.0$^{5,10}$]undecan-8-amine;

8-benzhydryl-N-(2-methoxy-5-trifluoromethoxybenzyl)-9-azatricyclo[4.3.1.0$^{4,9}$]decan-7-amine;

5,6-pentamethylene-2-benzhydryl-3-(2-methoxy-5-trifluoromethoxybenzyl)aminoquinuclidine;

5,6-trimethylene-2-benzhydryl-3-(2-methoxy-5-trifluoromethoxybenzyl)aminoquinuclidine;

9-benzhydryl-N-((2-methoxy-5-trifluoromethoxyphenyl) methyl)-3-oxa-10-azatricyclo[4.4.1.0$^{5,10}$]undecan-3-amine;

8-benzhydryl-N-((2-methoxy-5-trifluoromethoxyphenyl) methyl)-7-azatricyclo[4.4.1.0$^{5,10}$]undecan-9-amine; and 2-benzhydryl-N-((2-methoxy-5-trifluoromethoxyphenyl) methyl)-1-azabicyclo[3.2.2]nonan-3-amine.

The present invention also relates to a compound of the formula

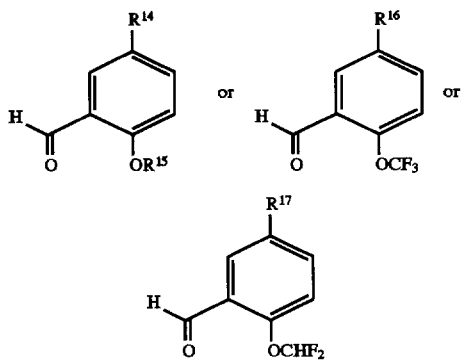

wherein R$^4$ trifluoromethoxy or difluoromethoxy, R$^{15}$ is (C$_1$–C$_4$) alkyl, R$^{16}$ is difluoromethoxy or (C$_1$–C$_4$)alkyl and R$^{17}$ is trifluoromethoxy, difluoromethoxy, (C$_1$–C$_4$)alkyl or (C$_1$–C$_4$) alkoxy.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

Formula I above includes compounds identical to those depicted but for the fact that one or more hydrogen or carbon atoms are replaced by radioactive isotopes thereof. Such radiolabelled compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like. Included among the radiolabelled forms of compounds of the formula I are the tritium and $C^{14}$ isotopes thereof.

DETAILED DESCRIPTION OF THE INVENTION

The compounds of the formula I may be prepared as described in the following reaction schemes and discussion. Unless otherwise indicated, $R^1$, $R^2$, $R^3$, $R^4$, $R^5$, $R^6$, $R^7$, $R^8$, $R^9$, $R^{10}$, $R^{11}$, $R^{12}$, $R^{13}$, X, Z, Q, Y, m, n, o, p, q, x, y, and z in the reaction schemes and discussion that follow are defined as above.

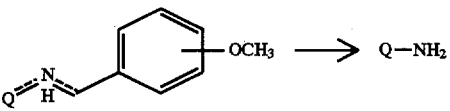

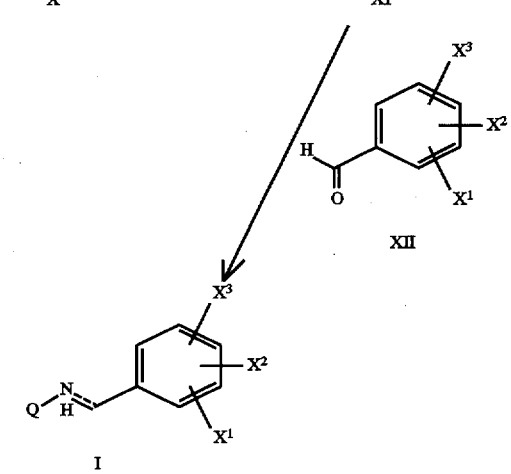

Scheme 2

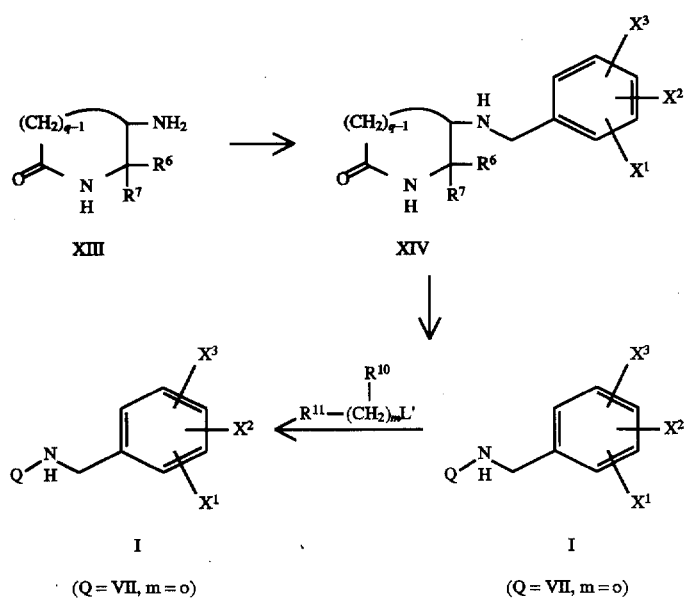

Scheme 3

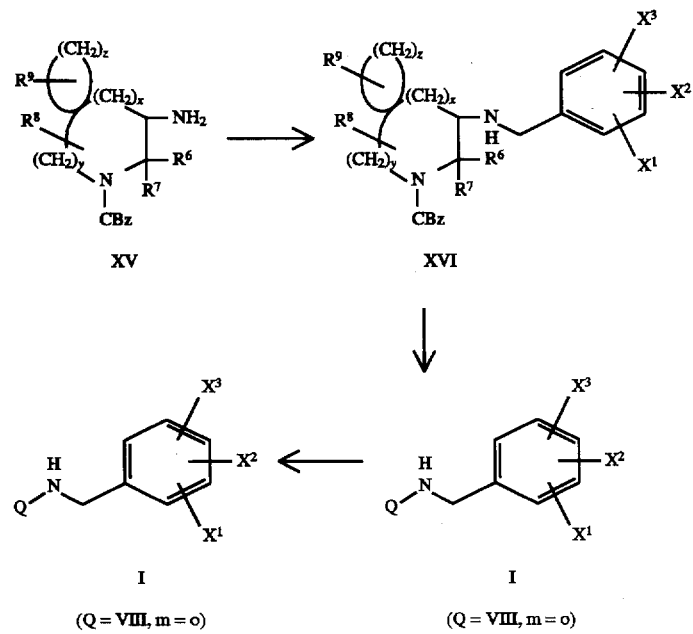

Compounds of the formula I may be prepared by the methods illustrated in schemes 1 and 2.

Referring to scheme 1, compounds of the formula X may be subjected to hydrolytic removal of the methoxybenzyl group using a strong mineral acid such as hydrochloric, hydrobromic or hydroiodic acid, at a temperature from about room temperature to about the reflux temperature of the acid. Preferably, the reaction is conducted in hydrobromic acid at the reflux temperature. This reaction, which yields the corresponding compounds of formula XI, is usually carried out for a period of about 2 hours.

For those compounds of the formula X wherein Q is a group of the formula VII or VIII, it is preferable to remove the methoxybenzyl group by treating them with hydrogen in the presence of a metal containing catalyst such as platinum or palladium. Generally, this reaction is conducted in a reaction inert solvent such as acetic acid or a lower alcohol, at a temperature from about 0° C. to about 50° C. (These compounds may also, alternatively, be treated with a dissolving metal such as lithium or sodium in ammonia at a temperature from about −30° C. to about −78° C., or with a formate salt in the presence of palladium or with cyclohexane in the presence of palladium). Preferably, such compounds are treated with hydrogen in the presence of palladium on carbon in a mixture of methanol/ethanol in water or methanol/ethanol containing hydrochloric acid at a temperature of about 25° C.

The resulting compounds of the formula XI may be converted to the corresponding compounds of the formula I by reaction with the appropriate compound of the formula XII (as depicted in scheme 1). This reaction is typically carried out in the presence of a reducing agent such as sodium cyanoborohydride, sodium triacetoxyborohydride, sodium borohydride, hydrogen and a metal catalyst, zinc and hydrochloric acid, borane dimethylsulfide or formic acid at a temperature from about −60° C. to about 50° C. Suitable reaction inert solvents for this reaction include lower alcohols (e.g., methanol, ethanol and isopropanol), acetic acid and tetrahydrofuran (THF). Preferably, the solvent is acetic acid, the temperature is about 25° C., and the reducing agent is sodium triacetoxyborohydride.

Alternatively, the reaction of a compound of the formula XI with a compound of the formula XII may be carried out in the presence of a drying agent or using an apparatus designed to remove azeotropically the water generated, to produce an imine of the formula

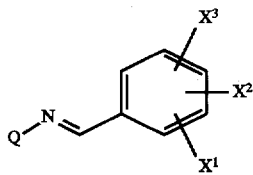

which is then reacted with a reducing agent as described above, preferably with sodium triacetoxyborohydride at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane, titanium isopropoxide/dichloromethane and molecular sieves/THF. Titanium tetrachloride/dichloromethane is preferred.

Compounds of the formula XI may also be converted to the corresponding compounds of the formula I by reaction with the appropriate compound of the formula

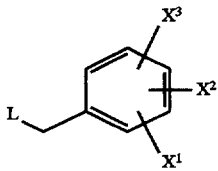

XII' wherein L is a leaving group (e.g., chloro, bromo, iodo, tosylate or mesylate). This reaction is generally carried out in a reaction inert solvent such as dichloromethane or THF, preferably dichloromethane, at a temperature from about 0° C. to about 60° C., preferably at about 25° C.

Compounds of the formula XI may also be converted to the corresponding compounds of the formula I by reacting them with the appropriate compound of the formula

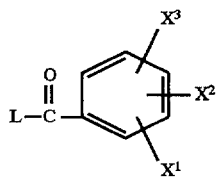

wherein L is defined as above or is imidazole, and then reducing the resulting amide. This reaction is typically carried out in an inert solvent such as THF or dichloromethane at a temperature from about −20° C. to about 60° C., preferably in dichloromethane at about 0° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

When Q is a group of the formula II, the starting materials of the formula X may be prepared as described in U.S. patent application Ser. No. 566,338, filed Jul. 20, 1990 and assigned to Pfizer Inc. This application is incorporated herein in its entirety.

When Q is a group of the formula III, the starting materials of the formula X may be prepared as described in U.S. patent application Ser. No. 532,525, filed Jun. 1, 1990 and the PCT patent application claiming priority from it that was filed Apr. 25, 1991 and is entitled "3-Amino-2-Aryl Quinuclidines." Both these applications are assigned to Pfizer Inc. and are incorporated herein in their entirety.

When Q is a group of the formula IV, V or VI, the starting materials of the formula X may be prepared as described in U.S. patent application Ser. No. 557,442, filed Jul. 23, 1990 and the PCT patent application claiming priority from it that was filed May 15, 1991, and is entitled "Quinuclidine Derivatives." Both these applications are assigned to Pfizer Inc. and are incorporated herein in their entirety.

When Q is a group of the formula VII, the starting materials of the formula X may be prepared as described in the following patent applications, all of which are assigned to Pfizer Inc: U.S. patent application Ser. No. 619,361, filed Nov. 28, 1990; U.S. patent application Ser. No. 675,244, filed Mar. 26, 1991; U.S. patent application Ser. No. 800,667, filed on Nov. 27, 1991; and PCT Patent Application Ser. No. PCT/US 92/00065, which designates the United States and was filed on Jan. 4, 1992. The foregoing four applications are incorporated herein in their entirety.

When Q is a group of the formula VIII, the starting materials of the formula X may be prepared as described in U.S. patent application Ser. No. 590,423, filed Sep. 28, 1990 and assigned to Pfizer Inc. This application is incorporated herein in its entirety.

Scheme 2 illustrates an alternate method of preparing compounds of the formula I wherein Q is a group of the formula VII.

As shown in Scheme 2, reductive amination of a compound of the formula XII with sodium cyanoborohydride or sodium triacetoxyborohydride and a compound of the formula XIII yields a compound of the formula XIV. This reaction is typically carried out in a polar solvent such as acetic acid or a lower alkanol, at a temperature from about 0° C. to about 50° C. Methanol is the preferred solvent and about 25° C. is the preferred temperature. It is also preferable that the pH of the reaction mixture be from about 4 to about 5.

Reduction of the compound of formula XIV yields a compound of the formula I wherein Q is a group of the formula VII and m is zero. Suitable reducing agents include borane dimethylsulfide in THF, lithium aluminum hydride, borane in THF and sodium borohydride-titanium (IV) chloride. Best results are obtained by using borane dimethylsulfide in THF. The reaction may be carried out at temperatures from about room temperature to about 150° C., and is preferably carried out at the reflux temperature of the solvent.

The compounds of formula I so formed may be converted to a compound of the formula I wherein Q is a group of the formula VII and m is other than zero having the same stereochemistry by reacting them with the appropriate compound of the formula $R^{10}$-$(CH_2)_m$-L', wherein L' is halo, mesylate or tosylate and wherein one of the carbon—carbon single bonds of said $(CH_2)_m$ may optionally be replaced by a carbon—carbon double bond or a carbon—carbon triple bond, and wherein one of the carbons of said $(CH_2)_m$ may optionally be substituted with $R^{11}$. This reaction is typically carried out in the presence of a base such as triethylamine or potassium t-butoxide, in a polar solvent such as methylene chloride or dichloroethane, and at a temperature from about room temperature to about 150° C. Preferably, the reaction is carried out at the reflux temperature in methylene chloride in the presence of triethylamine.

The starting materials of the formula XIII may be prepared as described in U.S. patent application Ser. No. 619,361, filed Nov. 28, 1990 and assigned to Pfizer Inc. This application is incorporated herein in its entirety.

Scheme 3 illustrates an alternate method of making compounds of the formula I wherein Q is a group of the formula VIII.

As shown in scheme 3, reductive amination of a compound of the formula XII in the presence of a compound of the formula XV yields a compound of the formula XVI. Examples of reducing agents that may be used are hydrogen in the presence of a metal catalyst, sodium borohydride, sodium cyanoborohydride and sodium triacetoxyborohydride. This reaction is generally carried out in a polar solvent such as acetic acid or a lower alkanol, in the presence of a dehydrating agent such as molecular sieves, at a temperature from about 0° to about 50° C. Methanol is the preferred solvent and 25° C. is the preferred temperature. It is also preferable that the pH of the reaction mixture be from about 4 to about 5.

Alternatively, compounds of the formula XVI may be formed by acylating a compound of the formula XV with a compound having the formula

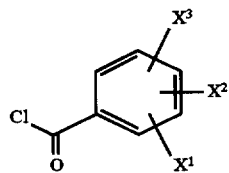

and then reducing the resulting amide. The acylation is generally conducted in a polar solvent (e.g., dichloromethane, THF or ethyl ether), at a temperature from about 0° to about 60° C. The preferred solvent is dichloromethane and the preferred temperature is about 25° C. Examples of reducing agents that may be used to reduce the amide are lithium aluminum hydride and borane dimethyl sulfide. The reduction is typically carried out in a polar solvent (e.g., ether, THF or DME) at a temperature from about 0° C. to about the reflux temperature of the solvent, preferably at about room temperature.

The compounds of formula XVI may be converted into the corresponding compounds of formula I wherein Q is a group of the formula VIII and m is zero by reacting them with ammonium formate in the presence of palladium on charcoal (e.g., 10% palladium on charcoal). Usually, a polar solvent such as ethyl acetate or a lower alkanol is used, and the reaction is run at a temperature from about room temperature to about 150° C. for about 0.5 to about 24 hours. Preferably, the reaction is conducted in ethanol at room temperature for about 3 to about 24 hours.

The compounds of the formula I prepared by the foregoing procedure may be converted into compounds that are identical but for the fact that m is not equal to zero using the procedure described above for preparing compounds of the formula I wherein Q is a group of the formula VII and m is not equal to zero.

The starting materials of the formula XV may be prepared as described in U.S. patent application Ser. No. 590,423, filed Sep. 28, 1990 and assigned to Pfizer Inc. This application is incorporated herein in its entirety.

Compounds of Formula I wherein Q is a group of the formula II and there is a double bond between Q and the adjacent nitrogen are prepared as shown below by condensation of Q=O (Q of formula II) with the appropriate benzylamine. The condensation is typically carried out in a nonhydroxylic solvent such as benzene, toluene or THF using an acid such as methanesulfonic acid or p-toluenesulfonic acid at a temperature from about 20° C. to the reflux temperature of the solvent. Preferably, the reaction is carried out using camphorsulfonic acid in toluene at reflux.

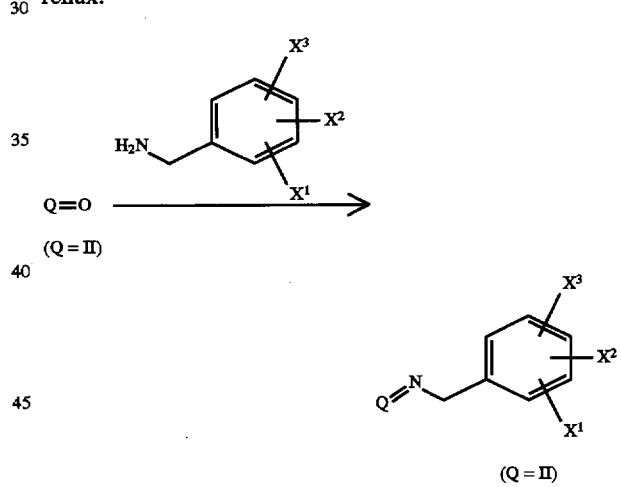

The preparation of other compounds of the formula I not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I which are also acidic in nature, e.g., where $R^1$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before.

In either case, stoichiometric quantities of reagents are preferably employed in order to ensure completeness of reaction and maximum yields of the desired final product. The compounds of formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission.

Such conditions include inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders may be determined by a study of their ability to suppress substance P-induced or substance P agonist induced hypermotility in guinea pigs. Such a study may be carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

2-(Diphenylmethyl)-N-((2-difluoromethoxy)phenyl)methyl-1-azabicyclo[2.2.2]octan-3-amine

A. 2-(Difluoromethoxy)benzaldehyde

To a 500 mL three-necked round-bottomed flask equipped with condenser and gas inlet tube were added 5.0 g (40.98 mmol) salicylaldehyde, 150 mL dioxane, and 150 mL (164 mmol) of a 1.1N aqueous solution of sodium hydroxide. Chlorodifluoromethane gas was bubbled through the reaction mixture as it was heated to 60° C., and the reaction mixture was stirred at this temperature for 2 hours. The reaction mixture was then cooled and extracted with ether. The organic layer was dried over sodium sulfate, filtered and evaporated. The residue was chromatographed on silica gel using hexane/ethyl acetate as eluant to afford a light yellow oil, 1.63 g (23%).

$^1$H NMR (δ, CDCl$_3$): 6.64 (t, J=72.7 (H—F), 1H), 7.16 (d, J=7, 1H), 7.24 (t, J=7, 1H), 7.53 (m, 1H), 7.81 (m, 1H), 10.29 (s, 1H). $^{13}$C-NMR (CDCl$_3$): 112.2, 115.6, 115.645, 115.7, 119.1, 119.2, 119.5, 125.6, 125.7, 125.8, 125.9, 127.5, 128.8, 128.9, 135.7, 152.71, 152.73, 188.4. IR (cm$^{-1}$, neat): 1700 (C=O). MS (%): 172 (100, parent), 171 (48), 122 (45), 121 (82), 120 (69), 104 (37), 95 (40), 92 (55), 91 (49), 76 (39), 65 (49), 63 (76), 51 (81). Anal. Calc'd for C$_8$H$_6$F$_2$O$_2$·¼H$_2$O: C 54.50, H 3.71. Found: C 54.68, H 3.33.

B. 2-(Diphenylmethyl)-N-((2-difluoromethoxy)phenyl)methyl-1-azabicyclo[2.2.2]octan-3-amine To a 25 mL round-bottomed flask equipped with a nitrogen inlet were added 500 mg (1.71 mmol) 2-diphenylmethyl-1-azabicyclo[2.2.2]octan-3-amine (prepared according to the method of Warawa, et al., *J. Med. Chem.*, 17, 497 (1974)), 8.5 mL methanol, 383 mg (2.23 mmol) 2-(difluoromethoxy)-benzaldehyde, and 216 mg (3.42 mmol) sodium cyanoborohydride. The reaction was stirred at room temperature for 30 hours, partitioned between ethyl acetate and water. The organic layer was separated, washed with brine, dried over sodium sulfate, and evaporated. To remove the last traces of unreacted amine, the mixture was treated with sodium triacetoxyborohydride in acetic acid at room temperature for 16 hours, then worked up with aqueous sodium hydroxide and methylene chloride. The residue was crystallized from isopropanol to afford a white solid, m.p. 144°–147° C., 206 mg (27%).

$^1$H NMR (δ, CDCl$_3$): 1.27 (m, 1H), 1.4–1.8 (m, 2H), 1.90 (m, 1H), 2.05 (m, 1H), 2.63 (m, 1H), 2.78 (m, 2H), 2.88 (m, 1H), 3.19 (m, 1H), 3.45 (AB$_q$, J$_{AB}$=13.5, Δν=105.5, 2H), 3.72 (dd, J=8, 12, 1H), 4.43 (d, J=12, 1H), 6.31 (t, J=74 (H—F), 1H), 6.55 and 7.0–7.4 (m, 14H). $^{13}$C-NMR (CDCl$_3$): 20.0, 24.9, 25.4, 42.0, 45.8, 49.4, 49.5, 55.0, 61.8, 116.3, 119.0, 125.4, 126.0, 126.5, 127.5, 127.8, 127.9, 128.0, 128.4, 128.5, 128.6, 129.1, 129.2, 130.0, 131.6, 143.2, 145.2, 149.3. IR (cm$^{-1}$, neat): 2940 (C—H), 1599 (C=C). MS (%): 449 (<1, parent+1), 291 (51), 281 (100), 84 (66), 49 (69). Anal. Calc'd for C$_{28}$H$_{30}$F$_2$N$_2$O: C 74.98, H 6.74, N 6.25. Found: C 74.72, H 6.70, N 6.23.

EXAMPLE 2

(2S,3S)-N-(2-Methoxy-5-trifluoromethoxyphenyl)methyl-2-diphenylmethyl-1-azabicyclo[2.2.2]octane-3-amine Methanesulfonic Acid Salt The title compound was prepared in a manner similar to he procedure described in Example 1, by replacing 2-(difluoromethoxy)benzaldehyde with 2-methoxy-5-trifluoromethoxybenzaldehyde in Step B.

M.p. 135° C. $^1$H NMR (CDCl$_3$) δ1.8–2.3 (m, 2H), 2.2–2.8 (m, 6H), 2.66 (s, 6H), 3.56 (s, 3H), 3.3–3.7 (m, 3H), 3.90 (m, 3H), 4.16 (m, 2H), 5.06 (m, 1H), 5.20 (br, 1H), 5.50 (m, 1H), 5.60 (br, 1H), 6.77 (d, 1H, J=9.2), 7.02 (m, 1H), 7.2–7.8 (m, 11H), 8.00 (br, 1H), 10.8 (br, 1H). IR (cm 1, KBr): 3180, 3140, 3000, 1500, 1200, 1062, 782.

EXAMPLE 3

(2S,3S)-2-Phenyl-3-[2-(2,2,2-trifluoroethoxy)benzyl]-aminopiperidine Hydrochloride

A. 2-(2,2,2-Trifluoroethoxy)benzaldehyde

Under a nitrogen atmosphere in a round-bottom flask equipped with a reflux condenser were placed 0.2 g (1 mmol) of 2-(2,2,2-trifluoroethoxy)benzonitrile (*J. Org. Chem.*, 377 (1983)) and 5 mL of formic acid. To this solution was added ca. 0.2 g of Raney nickel, and the mixture was heated at reflux for 90 minutes. The mixture was filtered through diatomaceous earth, and the filter cake was rinsed with water and chloroform (CHCl$_3$). The layers were separated, and the aqueous phase was extracted with three portions of chloroform. The combined organic fractions were washed with saturated aqueous sodium bicarbonate and water, dried over sodium sulfate (Na$_2$SO$_4$) and concentrated (rotary evaporator) to obtain 176 mg of the title compound as a yellow solid, m.p. 33°–34° C.

B. (2S,3S)-2-Phenyl-3-[2-(2,2,2-trifluoroethoxy)benzyl]aminopiperidine Hydrochloride Under a nitrogen atmosphere in a round-bottom flask were placed 112 mg (0.63 mmol) of (2S,3S)-3-amino-2-phenylpiperidine, 155 mg (0.76 mmol) of the aldehyde prepared in step A above and ca. 2 mL of acetic acid, and the solution was stirred at room temperature for 1 hour. To the system were added 294 mg (1.39 mmol) of sodium triacetoxyborohydride in portions, and the mixture was stirred at room temperature overnight. The mixture was concentrated with a rotary evaporator and partitioned between 1M aqueous sodium hydroxide (NaOH) and methylene chloride (CH$_2$Cl$_2$). The layers were separated, and the aqueous phase was extracted with three portions of CH$_2$Cl$_2$. The combined organic fractions were extracted with three portions of 2N aqueous HCl, the extracts were made basic with 2N aqueous NaOH, and the mixture was extracted with four portions of CH$_2$Cl$_2$. These CH$_2$Cl$_2$ extracts were dried (Na$_2$SO$_4$) and concentrated. The resulting oil was dissolved in ca. 2 mL ethyl acetate and treated with ether saturated with hydrogen chloride (HCl). The resulting white solid (73 mg, m.p.>275° C.) was collected. This material was converted to its free base by partitioning between 1N aqueous NaOH and CH$_2$Cl$_2$. The free base (58 mg) was purified by flash column chromatography eluting with chloroform (CHCl$_3$) followed by 1:19 methanol/CHCl$_3$ to obtain 32 mg of oil. Conversion of the free base to the corresponding hydrochloride salt as described above afforded 17 mg of the title compound, m.p.>275° C.

$^1$H NMR (free base, CDCl$_3$) δ1.44 (m, 1H), 1.63 (m, 1H), 1.88 (m, 1H), 2.1 (m, 1H), 2.80 (m, 2H), 3.26 (m, 1H), 3.38 (d, 1H, J=15), 3.66 (d, 1H, J=15), 3.88 (s, 1H), 4.08 (m, 2H), 6.68 (d, 1H, J=6), 6.90 (m, 1H), 6.98 (d, 1H, J=6), 7.16 (m, 1H), 7.26 (m, 5H). HRMS Calc'd for C$_{20}$H$_{24}$F$_3$N$_2$O$_3$ (parent+1): 365.1835. Found: 365. 1980. Anal. Calc'd for C$_{20}$H$_{23}$F$_3$N$_2$O.2HCl.½H$_2$O: C, 54.19, H, 5.84; N, 6.32. Found: C, 54.22, H, 5.57, N, 6.28.

EXAMPLE 4

(2S,3S)-3-(2-Methoxy-5-trifluoromethoxybenzyl)amino-2-phenylpiperidine Hydrochloride Salt

A. 2-Methoxy-5-trifluoromethoxybenzaldehyde

Under a nitrogen atmosphere in a round-bottom flask were placed 3.63 mL (28 mmol) of 4-trifluoromethoxyphenol and 25 mL of acetone. To this stirring solution were added 7.75 g (56 mmol) of potassium carbonate and 3.48 mL (56 mmol) of methyl iodide, and the reaction mixture was stirred at room temperature overnight. The solids were removed by suction filtration and the filter cake was rinsed with acetone. The filtrate was concentrated to obtain 6.5 g of a solid/oil mixture. This mixture was diluted with CHCl$_3$ and filtered and the filtrate was concentrated to afford 5.5 g of 1-methoxy-4-trifluoromethoxybenzene as a yellow oil.

$^1$H NMR (CDCl$_3$) δ3.78 (s, 3H), 6.83 (d, 1H, J=12), 7.10 (d, 1H, J=12). Mass spectrum m/z: 192 (parent).

Under a nitrogen atmosphere in a round-bottom flask were placed the 1-methoxy-4-trifluoromethoxybenzene (5.5 g, 29 mmol) and 110 mL of CH$_2$Cl$_2$. To the system, cooled in an ice/acetone bath, were added 3.77 mL (34 mmol) of titanium tetrachloride (TiCl$_4$) over a period of ca. 1 minute. The reaction mixture was stirred for 30 minutes and 5.69 mL (63 mmol) of α,α-dichloromethylmethyl ether was added to the system. The ice bath was allowed to expire and the mixture was stirred at room temperature overnight. The mixture was poured carefully into water and extracted with three portions of CH$_2$Cl$_2$. These combined extracts were washed with water and brine, dried (Na$_2$SO$_4$) and concentrated to obtain 6.06 g of an oil. The crude material was purified by flash column chromatography (250 g of silica gel) using 1:9 ethyl acetate/hexanes as the eluant to obtain 920 mg of the title compound with a slight impurity and 3.27 g of pure title compound.

$^1$H NMR (CDCl$_3$) δ3.94 (s, 3H), 7.00 (d, 1H, J=9), 7.38 (dd, 1H, J=3, 9), 7.66 (d, 1H, J=3), 10.4 (s, 1H). Mass spectrum m/z: 220 (parent).

B. (2S,3S)-3-(2-methoxy-5-trifluoromethoxybenzyl)amino-2-phenylpiperidine Hydrochloride Salt Under a nitrogen atmosphere in a round-bottom flask were placed 525 mg (2.4 mmol) of 2-methoxy-5-trifluoromethoxybenzaldehyde, 350 mg (2.0 mmol) of (2S,3S)-3-amino-2-phenylpiperidine and 5 mL of acetic acid. The reaction mixture was stirred at room temperature for 3 days and concentrated with a rotary evaporator. The residue was partitioned between 1N aqueous sodium hydroxide and chloroform (CHCl$_3$) and the mixture was extracted with three portions of chloroform. The combined chloroform extracts were extracted with three portions of 1N aqueous hydrochloric acid. The combined HCl extracts were made basic with concentrated aqueous sodium hydroxide and extracted with four portions of chloroform. The chloroform extracts were dried (Na$_2$SO$_4$) and concentrated with a rotary evaporator to obtain 760 mg of an oil. The oil was dissolved in ethyl acetate, and ether saturated with hydrogen chloride (HCl) was added to the solution. The resulting white solid was collected by suction filtration and washed with ether to obtain 600 mg of the title compound, m.p.>250° C.

$^1$H NMR (free base, CDCl$_3$) δ1.36 (s, 1H), 1.54 (m, 1H), 1.86 (m, 1H), 2.06 (m, 1H), 2.76 (m, 2H), 3.22 (m, 1H), 3.32 (d, 1H, J=15), 3.48 (s, 3H), 3.58 (d, 1H, J=15), 3.85 (d, 1H, J=3), 6.57 (d, 1H, J=9), 6.80 (d, 1H, J=3), 6.92 (dd, 1H, J=3, 9), 7.22 (m, 5H). HRMS Calc'd for $C_{20}H_{23}F_3N_2O_2$: 380.1711. Found: 380.1704. Anal. Calc'd for $C_{20}H_{23}F_3N_2O_2 \cdot 2HCl \cdot 0.2H_2O$: C 52.57, H 5.60,N 6.13. Found: C 52.58, H 5.40,N 5.97.

EXAMPLE 5

(2S,3S)-1-(5,6-Dimethoxyhexyl)-3-(2-methoxy-5-trifluoromethoxybenzyl)amino-2-phenylpiperidine Hydrochloride Under a nitrogen atmosphere in a round-bottom flask were placed 250 mg (0.66 mmol) of (2S,3S)-3-(2-methoxy-5-trifluoromethoxybenzyl)amino-2-phenylpiperidine, 2 mL of tetrahydrofuran (THF) and 0.28 mL (2.0 mmol) of triethylamine. To the system were added 475 mg (2.0 mmol) of 5,6-dimethoxy-1-methylsulfonyloxyhexane (prepared from 1,5,6-hexanetriol by sequential acetonide formation (acetone, p-toluenesulfonic acid), acetylation (acetyl chloride, triethylamine, THF), acetonide cleavage (60% acetic acid/water), dimethylation (sodium hydride, methyl iodide, THF), deacetylation (sodium methoxide, methanol) and methanesulfonate ester formation (methanesulfonyl chloride, triethylamine, THF)), and the mixture was heated at 50°–60° C. for four days. The reaction mixture was partitioned between $CHCl_3$ and saturated aqueous sodium bicarbonate and extracted with three portions of $CHCl_3$. The combined organic fractions were dried ($Na_2SO_4$), filtered and concentrated to obtain 853 mg of an orange oil. The crude material was purified by flash column chromatography (35 g of silica gel) using 1:19 methanol/chloroform as the eluant to obtain 185 mg of yellow oil. The oil was dissolved in ethyl acetate and ether saturated with HCl was added to the solution. The mixture was concentrated and the residue was triturated with ether to obtain 190 mg of the title compound.

$^1$H NMR (free base, $CDCl_3$) δ1.15 (m, 2H), 1.38 (m, 6H), 1.76 (m, 2H), 1.96 (m, 3H), 2.50 (m, 2H), 3.16 (m, 2H), 3.26 (m, 9H), 3.46 (s, 3H), 3.58 (d, 1H, J=15), 6.52 (d, 1H, J=9), 6.69 (m, 1H), 6.86 (m, 1H), 7.22 (m, 5H). HRMS calc'd for $C_{28}H_{39}F_3N_2O_4$: 524.28616. Found: 524.28634. Anal. Calc'd for $C_{28}H_{39}F_3N_2O_4 \cdot 2HCl \cdot 0.75H_2O$: C 55.03, H 7.00,N 4.58. Found: C 55.04, H 7.12,N 4.51.

EXAMPLE 6

(2S,3S)-2-Phenyl-3-(2-trifluoromethoxybenzyl) aminopiperidine Hydrochloride Salt Under a nitrogen atmosphere in a round-bottom flask were placed 3.0 mL (23 mmol) of trifluoromethoxybenzene and 25 mL of benzene. The system was cooled in ice/acetone bath, and 4.1 mL (45 mol) of α,α-dichloromethylmethyl ether was added to the stirring solution. To the system was added 6.13 g (46 mmol) of aluminum chloride ($AlCl_3$) in portions. After this addition was complete, the reaction mixture was allowed to warm gradually to room temperature and stirred at room temperature overnight. The reaction mixture was poured slowly into water and extracted with three portions of dichloromethane. The combined organic fractions were washed with water, dried ($Na_2SO_4$) and concentrated with a rotary evaporator to obtain 3.7 g of oil. This material, containing a mixture of 4- and 2-trifluoromethoxybenzaldehyde, was subjected to flash column chromatography (160 g of silica gel) using 1:49 ethyl acetate/hexanes as the eluant to obtain 500 mg of material enriched in 2-trifluoromethoxy-benzaldehyde.

Under a nitrogen atmosphere in a round-bottom flask were placed 155 mg (0.88 mmol) of (2S,3S)-3-amino-2-phenylpiperidine, the aldehyde obtained above and 2 mL of acetic acid. To the system were added 370 mg (1.8 mmol) of sodium triacetoxyborohydride and the mixture was stirred at room temperature overnight. The mixture was concentrated and the residue was partitioned between 1N aqueous sodium hydroxide and dichloromethane and extracted with three portions of dichloromethane. The combined organic fractions were extracted with three portions of 1N HCl. The acid extracts were made basic with 1N aqueous NaOH and extracted with three portions of dichloromethane. The dichloromethane extracts were dried and concentrated to afford 190 mg of oil, which was subjected to flash column chromatography (5 g of silica gel) using 1:9 methanol/chloroform as the eluant to obtain 95 mg of the free base of the title compound. The free base was dissolved in ethyl acetate, and ether saturated with HCl was added to the solution. The resulting white solid was collected by suction filtration and rinsed with ether to obtain 72 mg of the title compound, m.p. 231°–233° C.

$^1$H NMR (free base, $CDCl_3$) δ1.40 (m, 1H), 1.60 (m, 1H), 1.84 (m, 1H), 2.05 (m, 1H), 2.78 (m, 2H), 3.22 (m, 1H), 3.42 (d, 1H, J=15), 3.56 (d, 1H, J=15), 3.86 (d, 1H, J=3), 7.08 (m, 4H), 7.24 (m, 5H). Mass spectrum: m/z 350 (parent). Anal. Calc'd for $C_{19}H_{21}F_3N_2O \cdot 2HCl \cdot 0.25H_2O$: C 53.34, H 5.54,N 6.54. Found: C 53.19, H 5.40,N 6.54.

EXAMPLE 7

(2S,3S)-3-(2-Hydroxy-5-trifluoromethoxybenzyl) amino-2-phenylpiperidine Hydrochloride

A. 2-Hydroxy-5-trifluoromethoxybenzaldehyde

Under a nitrogen atmosphere, in a round-bottom flask were placed 300 mg (1.4 mmol) of 2-methoxy-5-trifluoromethoxybenzaldehyde and 30 ml of dichloromethane.

To the system, cooled in a dry ice acetone bath, were added 0.26 ml (2.7 mmol) of boron tribromide ($BBr_3$) over a period of ca. 1 minute. The reaction mixture was stirred for 1 hour, the dry ice/acetone bath was replaced with an ice bath and the mixture was stirred for 1 hour. To the system were added slowly 10 ml of saturated aqueous sodium bicarbonate followed by 10 ml of water, and the mixture was warmed to room temperature. The mixture was extracted with two portions of dichloromethane, and the extracts were dried ($Na_2SO_4$) and concentrated. The resulting oil (280 mg) was dissolved in $CH_2Cl_2$, and the solution was extracted with two portions of 1M aqueous NaOH. The combined aqueous extracts were acidified with 2M aqueous HCl and extracted with three portions of dichloromethane. These dichloromethane extracts were dried ($Na_2SO_4$) and concentrated to obtain 200 mg of the title compound.

$^1$H NMR ($CDCl_3$) δ6.96 (d, 1H, J=9), 7.36 (m, 2H), 9.84 (s, 1H), 10.9 (s, 1H).

B. (2S,3S)-3-(2-Hydroxy-5-trifluoromethoxybenzyl) amino-2-phenylpiperidine Hydrochloride The title compound was prepared in a manner similar to the compound of Example 4 by replacing 2-methoxy-5-trifluoromethoxybenzaldehyde with 2-hydroxy-5-trifluoromethoxybenzaldehyde.

$^1$H NMR (free base, $CDCl_3$) δ1.60 (m, 3H), 2.04 (m, 1H), 2.76 (m, 1H), 2.88 (m, 1H), 3.18 (m, 1H), 3.42 (s, 2H), 3.90 (m, 1H), 6.52 (m, 1H), 6.64 (d, 1H, J=9), 6.89 (m, 1H), 7.30 (m, 5H). HRMS calc'd for $C_{19}H_{21}F_3N_2O_2$: 366.1545. Found: 366.1562. Anal. calc'd for $C_{19}H_{21}F_3N_2O_2 \cdot 2HCl \cdot \frac{1}{2}H_2O$: C, 51.25; H, 4.90; N, 6.29. Found: C, 51.30; H, 4.75; N, 6.22.

EXAMPLE 8

(2S,3S)-3-(5-Chloro-2-[2,2,2-trifluoroethoxy] benzyl)amino-2-phenylpiperidine Hydrochloride A. 5-Chloro-2-(2,2,2-trifluoroethoxy)benzaldehyde Under a nitrogen atmosphere, in a round-bottom flask were placed 880 mg (22 mmol) of 60% sodium hydride (NaH) and 12 ml of N,N-dimethylformamide. To the system were added 2.9 ml (4 g, 40 mmol) of 2,2,2-trifluoroethanol via syringe over a period of 15 minutes and the mixture was stirred at room temperature for 20 minutes. To the system were added 1.72 g (10 mmol) of 2,5-dichlorobenzonitrile, and the mixture was heated at 90° C. for three days. The mixture was cooled to room temperature, poured into 50 ml of 2M aqueous HCl and extracted with three portions of ether. The combined organic fractions were dried ($Na_2SO_4$) and concentrated to afford 2.5 g of a solid. The crude material was purified by flash column chromatography using 1:49 ethyl acetate/hexanes as the eluant to obtain 1.4 g of 5-chloro-2-(2,2,2-trifluoroethoxy)benzonitrile as a white solid.

M.p. 61°–62° C.

Under a nitrogen atmosphere, in a round-bottom flask equipped with a reflux condenser were placed 400 mg (1.7 mmol) of the above nitrile and 10 ml of formic acid. To the system were added ca. 500 mg of Raney nickel and the mixture was heated at reflux for 6 hours and stirred at room temperature overnight. The mixture was filtered through a pad of a diatomaceous earth, and the pad was rinsed with water and $CHCl_3$. The layers were separated and the aqueous phase was extracted with three portions of $CHCl_3$. The combined organic fractions were dried and concentrated to obtain 270 mg of the title compound.

$^1H$ NMR ($CDCl_3$) $\delta 4.42$ (m, 2H), 6.86 (d, 1H, J=10), 7.46 (m, 1H), 7.80 (d, 1H, J=3), 10.3 (s, 1H). Mass spectrum: m/z 238 (parent).

B. (2S,3S)-3-(5-Chloro-2-[2,2,2-trifluoroethoxy] benzyl)amino-2-phenylpiperidine Hydrochloride The title compound was prepared in a manner similar to the procedure described in Example 4 by replacing 2-methoxy-5-trifluoromethoxybenzaldehyde with 5-chloro-2-(2,2,2-trifluoroethoxy)benzaldehyde.

M.p. 267°–269° C. $^1H$ NMR (free base, $CDCl_3$) $\delta 1.4$ (m, 1H), 1.6 (m, 1H), 1.82 (m, 1H), 2.02 (m, 1H), 2.78 (m, 2H), 3.2 (m, 1H), 3.3 (d, 1H, J=15), 3.54 (d, 1H, J=15), 3.84 (d, 1H, J=3), 4.0 (m, 2H), 6.54 (d, 1H, J=10), 6.92 (d, 1H, J=3), 7.04 (m, 1H), 7.24 (m, 5H). Anal. calc'd for $C_{20}H_{22}ClF_3N_2O \cdot 2HCl$: C, 50.91; H, 5.13; N, 5.94. Found: C, 50.89; H, 4.84; N, 5.93.

EXAMPLE 9

(2S,3S)-2-Phenyl-3-(3-trifluoromethoxybenzyl) aminopiperidine Hydrochloride

The title compound was prepared in a manner similar to the procedure described in Example 4 by replacing 2-methoxy-5-trifluoromethoxybenzaldehyde with 3-trifluoromethoxybenzaldehyde.

M.p.>275° C. $^1H$ NMR (free base, $CDCl_3$) $\delta 1.4$ (m, 1H), 1.56 (m, 1H), 1.78 (m, 1H), 1.96 (m, 1H), 2.76 (m, 2H), 3.18 (m, 1H), 3.30 (d, 1H, J=15), 3.46 (d, 1H, J=15), 3.84 (d, 1H, J=3), 6.79 (s, 1H), 6.85 (d, 1H, J=6), 6.94 (m, 1H), 7.12 (m, 1H), 7.24 (m, 5H). Anal. calc'd for $C_{19}H_{21}F_3N_2O_2 \cdot 2HCl$: C, 53.91; H, 5.48; N, 6.62. Found: C, 53.84; H, 5.07; N, 6.59.

The title compounds of Examples 10–23 and 26 were prepared in a manner similar to the procedure described in Example 4, by replacing 2-methoxy-5-trifluoromethoxybenzaldehyde with the appropriate aldehyde. Reaction sequences for the preparation of the requisite aldehydes are set forth in Table 1 below.

TABLE 1

Preparation of Compounds of the Formula XII

| —$C_6H_2X_1X_2X_3$ | Starting Material | Reaction* Sequence |
|---|---|---|
| 2-(2,2,2-trifluoroethoxy)phenyl | 2-chlorobenzonitrile | d, e |
| 2-hydroxy-5-trifluoromethoxyphenyl | 2-methoxy-5-trifluoromethoxybenzaldehyde | f |
| 3-trifluoromethoxyphenyl | — | commercial |
| 5-chloro-2-(2,2,2-trifluoroethoxy)-phenyl | 2,5-dichlorobenzonitrile | d, e |
| 5-t-butyl-2-trifluoromethoxyphenyl | trifluoromethoxybenzene | g, h |
| 2-ethoxy-5-trifluoromethoxyphenyl | 4-trifluoromethoxyphenol | i, a |
| 2-difluoromethoxy-5-trifluoromethoxyphenyl | 2-hydroxy-5-trifluoromethoxybenzaldehyde | j |
| 5-isopropyl-2-(2,2,2-trifluoroethoxy) phenyl | 4-isopropyl-iodobenzene | d, a |
| 2-isopropoxy-5-trifluoromethoxy phenyl | 4-trifluoromethoxyphenol | k, a |
| 5-t-butyl-2-difluoromethoxyphenyl | 4-t-butylphenol | a, j |
| 2,5-bis(difluoromethoxy)phenyl | 2,5-dihydroxybenzaldhyde | j |
| 2-difluoromethoxy-5-dimethylamino phenyl | 5-amino-2-hydroxybenzaldehyde | l, j |
| 2-difluoromethoxy-5-isopropylphenyl | 4-isopropylphenol | a, j |
| 2-difluoromethoxy-5-nitrophenyl | 2-hydroxy-5-nitrobenzaldehyde | j |
| 5-dimethylamino-2-(2,2,2-trifluoro-ethoxy)phenyl | 2-chloro-5-nitrobenzonitrile | d, l, e |
| 5-acetamido-2-(2,2,2-trifluoro- | 5-nitro-2-(2,2,2-trifluoroethoxy)- | m, c, e |

TABLE 1-continued

Preparation of Compounds of the Formula XII

| —$C_6H_2X_1X_2X_3$ | Starting Material | Reaction* Sequence |
|---|---|---|
| ethoxy)phenyl | benzonitrile | |
| 2-difluoromethoxy-5-ethylphenyl | 4-ethyl-methoxybenzene | a, f, j |
| 5-chloro-2-difluoromethoxyphenyl | 5-chloro-2-hydroxybenzaldehyde | j |
| 2-trifluoromethoxyphenyl | commercial | |
| 2-methoxy-5-trifluoromethoxyphenyl | 4-trifluoromethoxyphenol | b, a |
| 2-difluoromethoxy-5-methylphenyl | 5-methyl-2-methoxybenzaldehyde | f, j |

*Reagents for Preparation of Compounds of the Formula XII
From Standard Routes
a) $Cl_2CHOCH_3$, $TiCl_4$
b) methyl iodide
c) acetyl chloride
d) $NaOCH_2CF_3$
e) Raney nickel, $HCO_2H$
f) $BBr_3$
g) t-butyl chloride/$AlCl_3$
h) $Cl_2CHOCH_3$/$AlCl_3$
i) ethyl iodide
j) $ClF_2CH$
k) isopropyl bromide
l) $H_2$, Pd/C, HCHO
m) $H_2$-Pd/$BaSO_4$

EXAMPLE 10

(2S 3S)-3-[5-Chloro-2-(2,2,2-trifluoroethoxy) benzyl]amino-2-phenylpiperidine Hydrochloride M.P. 267°–269° C. $^1$H NMR (free base; $CDCl_3$) δ1.40 (m, 1H), 1.60 (m, 1H), 1.82 (m, 1H), 2.02 (m, 1H), 2.76 (m, 2H), 3.20 (m, 1H), 3.28 (d, 1H, J=15), 3.52 (d, 1H, J=15), 3.84 (d, 1H, J=3), 4.00 (m, 2H), 6.54 (d, 1H, J=10), 6.92 (d, 1H, J=3), 7.04 (m, 1H), 7.24 (m, 5H). HRMS calc'd for $C_{20}H_{22}ClF_3N_2O$: 398.1368. Found: 398.1352. Anal. calc'd for $C_{20}H_{22}ClF_3N_2O\cdot2HCl$: C, 50.91; H, 5.13; N, 5.94. Found: C, 50.89; H, 4.84; N, 5.93.

EXAMPLE 11

(2S,3S)-3-(5-t-Butyl-2-trifluoromethoxybenzyl) amino-2-phenylpiperidine Hydrochloride M.P. 262°–264° C. $^1$H NMR (free Base; $CDCl_3$) δ1.20 (s, 9H), 1.40 (m, 1H), 1.52 (m, 1H), 1.84 (m, 1H), 2.06 (m, 1H), 2.80 (m, 2H), 3.22 (m, 1H), 3.38 (d, 1H, J=15), 3.58 (d, 1H, J=15), 3.86 (d, 1H, J=3), 6.98 (m, 1H), 7.12 (m, 2H), 7.26 (m, 5H). HRMS calc'd for $C_{23}H_{29}F_3N_2O$: 406.2225. Found: 406.2271. Anal. calc'd for $C_{23}H_{29}F_3N_2O\cdot2HCl\cdot\frac{1}{3}H_2O$: C, 56.92; H, 6.56; N, 5.77. Found: C, 56.99; H, 6.41; N, 6.03.

EXAMPLE 12

(2S,3S)-3-[5-Isopropyl-2-(2,2,2-trifluoroethoxy) benzyl]amino-2-phenylpiperidine Hydrochloride M.P.>280° C. $^1$H NMR (free base; $CDCl_3$) δ1.12 (m, 6H), 1.4 (m, 1H), 1.62 (m, 1H), 1.82 (m, 1H), 2.08 (m, 1H), 2.76 (m, 3H), 3.22 (m, 1H), 3.30 (d, 1H, J=15), 3.38 (d, $^1$H, J=15), 3.82 (d, 1H, J=3), 4.02 (m, 2H), 6.56 (d, 1H, J=10), 6.78 (d, 1H, J=3), 6.94 (m, 1H), 7.24 (m, 5H). HRMS calc'd for $C_{23}H_{30}F_3N_2O$ (M+1): 407.2303. Found: 407.2287. Anal. calc'd for $C_{23}H_{29}F_3N_2O\cdot2HCl\cdot\frac{1}{2}H_2O$: C, 56,55, H, 6.60; N, 5.70. Found: C, 56.17: H, 6.39; N, 5.77.

EXAMPLE 13

(2S,3S)-3-[5-Dimethylamino-2-(2,2,2-trifluoroethoxy)benzyl]amino-2-phenylpiperidine Hydrochloride M.P. 250°–252° C. $^1$H NMR (free base; $CDCl_3$) δ1.40 (m, 1H), 1.60 (m, 1H), 1.86 (m, 1H), 2.10 (m, 1H), 2.82 (m, 8H), 3.22 (m, 1H), 3.34 (d, 1H, J=15), 3.58 (d, 1H, J=15), 3.88 (d, 1H, J=3), 4.00 (m, 2H), 6.42 (d, 1H, J=3), 6.50 (m, 1H), 6.64 (d, 1H, J=10), 7.30 (m, 5H). HRMS calc'd for $C_{22}H_{28}F_3N_3O$: 407.2178. Found: 407.2179.

EXAMPLE 14

(2S 3S)-3-(2-Difluoromethoxy-5-N,N-dimethylaminobenzyl)amino-2-phenylpiperidine Hydrochloride M.P. 243°–245° C. (dec). $^1$H NMR (free base; $CDCl_3$) δ1.44 (m, 1H), 1.72 (m, 2H), 2.10 (m, 1H), 2.84 (m, 8H), 3.21 (m, 1H), 3.28 (d, 1H, J=15), 3.55 (d, 1H, J=15), 3.88 (d, 1H, J=3), 6.08 (t, 1H, J=72), 6.36 (d, 1H, J=3), 6.46 (dd, 1H, J=3,9), 6.86 (d, 1H, J=9), 7.28 (m, 5H). HRMS calc'd for $C_{21}H_{27}F_2N_3O$: 375.2122. Found: 375.2138. Anal. calc'd for $C_{21}H_{27}F_2N_3O\cdot3HCl\cdot\frac{1}{2}H_2O$: C, 51.07; H, 6.44; N, 8.51. Found: C, 50.71; H, 6.08; N, 8.28.

EXAMPLE 15

(2S,3S)-3-[2,5-bis(difluoromethoxy)benzyl]amino-2-phenylpiperidine Hydrochloride M.P. 238°–239° C. $^1$H NMR (free base; $CDCl_3$) δ1.64 (m, 3H), 2.04 (m, 1H), 2.76 (m, 2H), 3.18 (m, 1H), 3.28 (d, 1H, J=12), 3.52 (d, 1H, J=12), 3.84 (d, 1H, J=3), 6.12 (t, 1H, J=75), 6.40 (t, 1H, J=75), 6.75 (m, 2H), 6.94 (d, 1H, J=9), 7.24 (m, 5H). HRMS calc'd for $C_{20}H_{22}F_4N_2O_2$: 398.1612 Found: 398.1591.

EXAMPLE 16

(2S,3S)-3-(5-t-Butyl-2-difluoromethoxybenzyl) amino-2-phenylpiperidine Hydrochloride M.P. 263°–264° C. (dec). $^1$H NMR (free base; $CDCl_3$) δ1.24 (s, 9H), 1.42 (m, 1H), 1.62 (m, 1H), 1.80 (m, 1H), 2.10 (m, 1H), 2.80 (m, 2H), 3.24 (m, 2H), 3.58 (d, 1H, J=12), 3.87 (brs, 1H), 6.18 (t, 1H, J=72), 6.86 (d, 1H, J=6), 7.00 (brs, 1H), 7.12 (m, 1H), 7.24 (m, 5H). HRMS calc'd for $C_{23}H_{30}F_2N_2O$: 388.2321. Found: 388.2336.

EXAMPLE 17

(2S,3S)-3-(2-Isopropoxy-5-trifluoromethoxybenzyl)amino-2-phenylpiperidine Hydrochloride M.P. 245°–246° C. (dec). $^1$H NMR (free base: CDCl$_3$) δ1.08 (d, 3H, J=6), 1.12 (d, 3H, J=6), 1.40 (m, 1H), 1.64 (m, 1H), 1.87 (m, 1H), 2.08 (m, 1H), 2.78 (m, 2H), 3.02 (m, 1H), 3.34 (d, 1H, J=15), 3.51 (d, 1H, J=15), 3.85 (d, 1H, J=2), 4.28 (m, 1H), 6.01 (d, 1H, J=9), 6.82 (m, 1H), 6.91 (m, 1H), 7.24 (m, 5H). HRMS calc'd for C$_{22}$H$_{27}$F$_3$N$_2$O$_2$: 408.2024. Found: 408.2019. Anal. calc'd for C$_{22}$H$_{27}$F$_3$N$_2$O$_2$.2HCl: C, 54.89; H, 6.07, N, 5.82. Found: C, 54.50; H, 6.24; N, 5.78.

EXAMPLE 18

(2S,3S)-3-(2-Difluoromethoxy-5-trifluoromethoxybenzyl)amino-2-phenylpiperidine Hydrochloride M.P. 257°–259° C. (dec). $^1$H NMR (free base; CDCl$_3$) δ1.44 (m, 1H), 1.58 (m, 1H), 1.78 (m, 1H), 2.03 (m, 1H), 2.78 (m, 2H), 3.20 (m, 1H), 3.32 (d, 1H, J=15), 3.54 (d, 1H, J=15), 3.87 (d, 1H, J=2), 6.15 (t, 1H, J=72), 6.94 (m, 3H), 7.26 (m, 5H). HRMS calc'd for C$_{20}$H$_{21}$F$_5$N$_2$O$_2$: 416.1523. Found: 416.1501. Anal. calc'd for C$_{20}$H$_{21}$F$_5$N$_2$O$_2$.2HCl.⅓H$_2$O: C, 48.50; H, 4.81; N, 5.65. Found: C, 48.45; H, 4.57; N, 5.66.

EXAMPLE 19

(2S,3S)-3-(2-Ethoxy-5-trifluoromethoxybenzyl)amino-2-phenylpiperidine Hydrochloride M.P.>275° C. (dec). $^1$H NMR (free base; CDCl$_3$) δ1.13 (t, 3H, J=6), 1.38 (m, 1H), 1.70 (m, 2H), 2.06 (m, 1H), 2.74 (m, 2H), 3.22 (m, 1H), 3.30 (d, 1H, J=15), 3.68 (m, 3H), 3.84 (br s, 1H), 6.55 (d, 1H, J=9), 6.79 (br s, 1H), 6.90 (m, 1H), 7.2 (m, 5H). HRMS calc'd for C$_{21}$H$_{25}$F$_3$N$_2$O$_2$: 394.1868. Found: 394.1875. Anal. calc'd for C$_{21}$H$_{25}$F$_3$N$_2$O$_2$.2HCl: C, 53.97; H, 5.82; N, 6.00. Found: C, 53.85; H, 5.79; N, 5.95.

EXAMPLE 20

(2S,3S)-3-(2-Difluoromethoxy-5-nitrobenzyl)amino-2-phenylpiperidine Hydrochloride $^1$H NMR (free base; CDCl$_3$) δ1.50 (m, 1H), 1.66 (m, 1H), 1.98 (m, 2H), 2.82 (m, 2H), 3.28 (m, 1H), 3.42 (d, 1H, J=15), 3.64 (d, 1H, J=15), 3.95 (d, 1H, J=2), 6.30 (t, 1H, J=72), 7.08 (d, 1H, J=8), 7.30 (m, 5H), 8.04 (m, 2H). FAB HRMS calc'd for C$_{19}$H21F$_2$N$_3$O$_3$(M+1): 378.1629. Found: 378.1597.

EXAMPLE 21

(2S,3S)-3-(2-Difluoromethoxy-5-isopropylbenzyl)amino-2-phenylpiperidine Hydrochloride M.P. 245°–247° C. (dec). $^1$H NMR (free base; CDCl$_3$) δ1.19 (2d, 6H, J=7), 1.50 (m, 1H), 1.75 (m, 2H), 2.12 (m, 1H), 2.83 (m, 3H), 3.25 (m, 1H), 3.35 (d, 1H, J=14), 3.60 (d, 1H, J=14), 3.90 (d, 1H, J=3), 6.20 (t, 1H, J=75), 6.90 (m, 21H), 7.00 (m, 1H), 7.30 (m, 5H). HRMS calc'd for C$_{22}$H$_{28}$F$_2$N$_2$O: 374.2170. Found: 374.2207. Anal. calc'd for C$_{22}$H$_{28}$F$_2$N$_2$O.2HCl.⅓H$_2$O: C, 58.28; H, 6.67; N, 6.18. Found: C, 58.17; H, 6.52; N, 6.17.

EXAMPLE 22

(2S,3S)-3-[5-Acetamido-2-(2,2,2-trifluoroethoxy)benzyl]amino-2-phenylpiperidine Hydrochloride M.P.>270° C. $^1$H NMR (free base; CDCl$_3$) δ1.46 (m, 1H), 1.82 (m, 1H), 2.08 (m, 1H), 2.12 (s, 3H), 2.76 (m, 2H), 3.20 (m, 1H), 3.48 (d, 1H, J=15), 3.58 (d, 1H, J=15), 3.82 (m, 1H), 4.08 (m, 2H), 6.44 (m, 1H), 6.58 (d, 1H, J=10), 6.78 (m, 1H), 7.26 (m, 5H), 7.58 (m, 1H).

EXAMPLE 23

(2S,3S)-3-(2-Difluoromethoxy-5-ethylbenzyl)amino-2-phenylpiperidine Hydrocholoride M.P. 254°–255° C. $^1$H NMR (free base; CDCl$_3$) δ1.12 (t, 3H, J=10), 1.36 (m, 1H), 1.44 (m, 1H), 1.82 (m, 1H), 2.10 (m, 1H), 2.48 (q, 2H, J=10), 2.8 (m, 1H), 3.10 (m, 1H), 3.34 (d, 1H, J=15), 3.58 (d, 1H, J=15), 3.9 (d, 1H, J=3), 6.12 (t, 1H, J=85), 6.78 (s, 1H), 6.90 (m, 2H), 7.28 (m, 5H). Anal. calc'd for C$_{21}$H$_{26}$F$_2$N$_2$O.2HCl: C, 58.19; H, 6.51; N, 6.47. Found: C, 57.90; H, 6.52; N, 6.64.

EXAMPLE 24 cis-3-(5-t-Butyl-2-methoxybenzyl)amino-2-(3-trifluoromethoxyphenyl)piperidine Hydrochloride A. cis-5-Nitro-6-(trifluoromethoxyphenyl)piperidin-2-one Under a nitrogen atmosphere, in a round-bottom flask were placed 15 g (79 mmol) of 3-trifluoromethoxybenzaldehyde, 80 mL of ethanol, 11 g (0.26 mol) of ammonium acetate and 12.6 mL (79 mmol) of methyl 4-nitrobutyrate, and the mixture was heated at reflux for 6 hours. After cooling to room temperature, the mixture was concentrated. The remaining material was stirred with ca. 200 mL of CHCl$_3$ for 30 minutes, filtered and concentrated. The residue purified by flash column chromatography, eluting with 1:49 methanol/chloroform followed by 1:19 methanol/chloroform to obtain 24 g of 5-nitro-6-(3-trifluoromethoxyphenyl)piperidin-2-one.

In a round bottom flask were placed 20 g (66 mmol) of the product obtained above, 13 g of KOH and 100 mL of ethanol, and the mixture was stirred at room temperature for 90 minutes. To the system was added ca. 35 mL of 33% sulfuric acid/ethanol. The mixture was poured into 150 mL of water and extracted with three 100 mL portions of CHCl$_3$. The combined extracts were washed with water, dried (Na$_2$SO$_4$) and concentrated. The crude material was purified by column chromatography (300 g of silica gel) using ethyl acetate followed by 1:99 methanol/ethyl acetate as the eluant to obtain 5.8 g of cis-5-nitro-6-(3-trifluoromethoxyphenyl)piperidin-2-one which contained ca. 12% of the corresponding trans-isomer. This material was purified by a second chromatography to obtain 4.6 g of the cis-product.

B. cis-5-Amino-6-(3-trifluoromethoxyphenyl)piperidin-2-one

Under a nitrogen atmosphere, in a three-neck round-bottom flask equipped with a thermometer and a mechanical stirrer, were placed this cis-material and a mixture of THF (200 mL), methanol (50 mL) and water (5 mL). To this stirring solution was added aluminum amalgam (prepared by washing 4.1 g of aluminum foil strips with ether and dipping in 2% aqueous HgCl$_2$ for 30–45 seconds and washing with ether), and the mixture was stirred at room temperature overnight. The mixture was filtered through a pad of diatomaceous earth and the pad washed with THF. The filtrate was concentrated, dissolved in ethyl acetate and treated with 30 mL of ether saturated with HCl. Concentration afforded 3.7 g of crude cis-5-amino-6-(3-trifluoromethoxyphenyl)piperidin-2-one as a waxy solid, m.p. 126°–130° C.

C. cis-3-(5-t-Butyl-2-methoxybenzyl)amino-2-(3-trifluoromethoxyphenyl)piperidine Hydrochloride Under a nitrogen atmosphere, in a round-bottom flask were placed 0.38 g (1.4 mmol) of the amine obtained above, 6 mL of acetic acid and 0.32 g (1.66 mmol) of 5-t-butyl-2-methoxybenzaldehyde. The mixture was stirred for 45 minutes. To the system was added 0.65 g (3.0 mmol) of sodium triacetoxyborohydride in portions, and the mixture was stirred at room temperature overnight. The mixture was concentrated and partitioned between chloroform and $H_2O$ and made basic with 1N aqueous NaOH. The layers were separated and the aqueous phase was extracted with two portions of $CHCl_3$. The combined organic fractions were washed with $H_2O$, dried and concentrated. The crude product was purified by flash column chromatography to obtain 0.4 g of cis-5-(5-t-butyl-2-methoxybenzyl)amino-6-(3-trifluoromethoxyphenyl)piperidin-2-one.

Under a nitrogen atomsphere, in a round-bottom flask were placed 0.4 g (0.9 mmol) of the product obtained above and 10 mL of THF. To the system was added 2.2 mL (4.4 mmol) of 2M borane methyl sulfide complex in THF and the mixture was gradually heated and allowed to reflux for 4 hours. The mixture was cooled to room temperature, 2 mL of methanol was added to the system and the mixture was concentrated. To the system was added 5 mL of ethanol and 2.45 of $K_2CO_3$, and the mixture was heated at reflux for 8 hours and stirred at room temperature overnight. The mixture was concentrated and partitioned between water and $CH_2Cl_2$. The layers were separated, and the aqueous phase was extracted with three portions of $CH_2Cl_3$. The combined organic fractions were dried and concentrated to obtain an oil. The oil was dissolved in ethyl acetate, and the solution was treated with ether saturated with HCl. Concentration afforded 70 mg of the title compound as a waxy solid.

M.P. 247° C.–249° C. $^1$H NMR (free-base, $CDCl_3$) δ1.26 (s, 9H), 1.6 (m, 1H), 1.90 (m, 2H), 2.12 (m, 1H), 2.80 (m, 2H), 3.24 (m, 1H), 3.36 (d, 1H, J=15), 3.48 (s, 3H), 3.64 (d, 1H, J=15), 3.86 (m, 1H), 6.60 (d, 1H, J=10), 7.18 (m, 6H). HRMS Calc'd: $C_{24}H_{31}N_2O_2F_3$: 436.2330. Found: 436.2326.

EXAMPLE 25 cis-2-(3 5-Dibromophenyl)-3-(2-methoxy-5-trifluoromethoxybenzyl)aminopiperidine The title compound was prepared by a procedure similar to that described in Example 25, with the exception that the nitro substituent of the product of the initial reaction [6-(3,5-dibromophenyl)-5-nitropiperidin-2-one] was converted to an amino group by sequential oxidative cleavage ($O_3$, KO$^+$Bu), oxime formation ($H_2$NOH) and Raney nickel-catalyzed reduction. The final product can be resolved by treatment with (R)-(–)-mandelic acid in isopropanol. Two recrystallizations of the solid isolated from this procedure (isopropanol), followed by treatment with saturated aqueous sodium bicarbonate affords the (2S,3S)-enantiomer; [α]$_D$ (mandelate salt): +4.11° (MeOH, c=0.51).

$^1$H NMR ($CDCl_3$) δ1.36 (m, 1H), 1.50 (m, 1H), 1.80 (m, 1H), 2.04 (m, 1H), 2.70 (m, 2H), 3.18 (m, 1H), 3.30 (d, 1H, J=18), 3.57 (s, 3H), 3.66 (d, 1H, J=18), 3.75 (m, 1H), 6.63 (d, 1H, J=9), 6.86 (d, 1H, J=3), 6.97 (dd, 1H, J=6, 9), 7.32 (m, 2H), 7.48 (s, 1H)).

EXAMPLE 26

(2S-3S)-3-(2-Difluoromethoxy-5-methylbenzyl)amino-2-phenylpiperidine Hydrochloride The title compound was prepared by a procedure similar to that described in Example 4.

M.P.>275° C. $^1$H NMR (free-base, $CDCl_3$) δ1.44 (m, 1H), 1.6 (m, 1H), 1.84 (m, 1H), 2.10 (m, 1H), 2.20 (s, 3H), 2.80 (m, 2H), 3.22 (m, 1H), 3.34 (d, 1H, J=15), 3.58 (d, 1H, J=15), 3.90 (d, 1H, J=3), 6.10 (t, 1H, J=72), 6.84 (m, 2H), 7.26 (m, 5H). HRMS calc'd for $C_{20}H_{24}F_2N_2O$: 347.1929 (M+1). Found: 347.1911. Anal. calc'd for $C_{20}H_{24}F_2N_2O \cdot 2HCl \cdot 0.25H_2O$: C, 56.67; H, 6.30; N, 6.61. Found: C, 56.81; H, 6.16; N, 6.50.

We claim:

1. A compound of formula

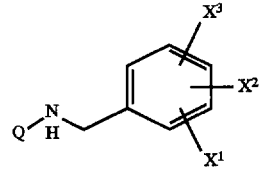

wherein $X^1$ is hydrogen, ($C_1$–$C_{10}$) alkoxy optionally substituted with from one to three fluorine atoms or ($C_1$–$C_{10}$) alkyl optionally substituted with from one to three fluorine atoms;

$X^2$ and $X^3$ are independently selected from halo, hydrogen, nitro, ($C_1$–$C_{10}$) alkyl optionally substituted with from one to three fluorine atoms, ($C_1$–$C_{10}$) alkoxy optionally substituted with from one to three fluorine atoms, trifluoromethyl, hydroxy, phenyl, cyano, amino, ($C_1$–$C_6$)-alkylamino, di-($C_1$–$C_6$)alkylamino, —C(=O)—NH—($C_1$–$C_6$) alkyl, ($C_1$–$C_6$) alkyl-C(=O)—NH—($C_1$–$C_6$) alkyl, hydroxy($C_1$–$C_4$)alkyl, ($C_1$–$C_4$)alkoxy($C_1$–$C_4$)alkyl, —NHC(=O)H and —NHC(=O)—($C_1$–$C_6$) alkyl; and Q is a group of the formula

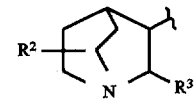

wherein $R^2$ is hydrogen or ($C_1$–$C_6$) alkyl;

$R^3$ is phenyl, biphenyl, naphthyl, pyridyl, benzhydryl, thienyl or furyl, and $R^3$ may optionally be substituted with from one to three substituents independently selected from halo, ($C_1$–$C_{10}$) alkyl optionally substituted with from one to three fluorine atoms and ($C_1$–$C_{10}$) alkoxy optionally substituted with from one to three fluorine atoms;

with the proviso that when neither $X^1$, $X^2$ nor $X^3$ is a fluorinated alkoxy group, $R^3$ is an aryl group substituted with a fluorinated alkoxy group.

2. A compound according to claim 1 wherein Q is a group of the formula III, $R^2$ is hydrogen and $R^3$ is phenyl or substituted phenyl.

3. A compound according to claim 1, wherein said compound is 2-(diphenylmethyl)-N-((2-difluoromethoxy)phenyl)methyl-1-azabicyclo[2.2.2]octan-3-amine.

4. A compound according to claim 1, wherein said compound is (2S,3S)-N-(2-methoxy-5-trifluoromethoxyphenyl)methyl-2-diphenylmethyl-1-azabicyclo[2.2.2]octane-3-amine.

5. A compound according to claim 1, wherein $X^1$ is 5-trifluoromethoxy, $X^2$ is hydrogen and $X^3$ is 2-methoxy.

6. A compound according to claim 1 wherein $X^1$ is 2-trifluoromethoxy and each of $X^2$ and $X^3$ is hydrogen.

7. A compound according to claim 1, wherein $X^1$ is 2-(2,2,2-trifluoroethoxy) and each of $X^2$ and $X^3$ is hydrogen.

8. A compound according to claim 1 wherein Q is a group of the formula

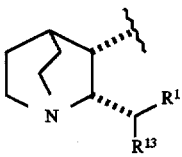

wherein $R^1$ and $R^{13}$ are each independently selected from unsubstituted or substituted phenyl, $X^1$ is 2-trifluoromethoxy, 2-methoxy or 2-(2,2,2-trifluoroethoxy), and $X^2$ is 5-halo, 5-($C_1$–$C_6$)alkyl or 5-($C_1$–$C_6$) alkoxy optionally substituted with from one to three fluorine atoms.

9. A compound according to claim 1 having the formula

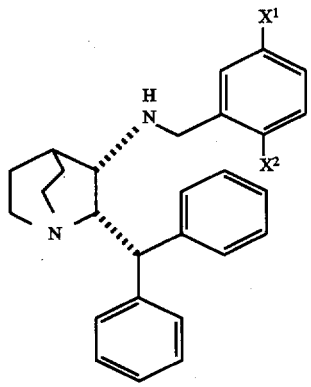

wherein $X^1$ is ($C_1$–$C_4$) alkyl or hydrogen, $X^2$ is $OCF_3$ or $OCHF_2$, and one or both of the phenyl moieties of the benzhydryl group may be optionally substituted with a substituent selected from ($C_1$–$C_4$)alkyl, ($C_1$–$C_4$)alkoxy, fluorine and chlorine.

10. A compound according to claim 1 having the formula

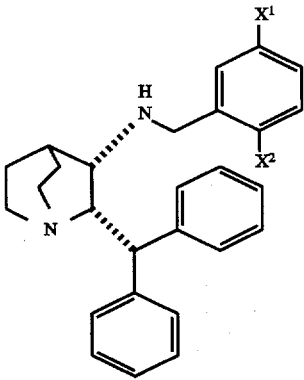

wherein $X^1$ is $OCF_3$ or $OCHF_2$, $X^2$ is ($C_1$–$C_4$)alkoxy, and one or both of the phenyl moieties of the benzhydryl group may be optionally substituted with a substituent selected from ($C_1$–$C_4$)alkyl, ($C_1$–$C_4$)alkoxy, fluorine and chlorine.

11. A compound according to claim 1, wherein $X^1$ is a 2-($C_1$–$C_4$)alkoxy group, $X^2$ is hydrogen and $X^3$ is a 5-$OCF_3$ or 5-$OCHF_2$ group.

12. A compound according to claim 1, wherein $X^1$ is a 2-$OCF_3$ or 2-$OCHF_2$ group, $X^2$ is hydrogen and $X^3$ is ($C_1$–$C_4$)alkyl.

13. A pharmaceutical composition for treating a condition selected from the group consisting of inflammatory diseases, anxiety, colitis, depression or dysthymic disorders, psychosis, pain, gastroesophageal reflux disease, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in treating such condition and a pharmaceutically acceptable carrier.

14. A method of treating a condition selected from the group consisting of inflammatory diseases anxiety, colitis, depression or dysthymic disorders, psychosis, pain, gastroesophageal reflux disease, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment an amount of a compound according to claim 1 effective in treating such condition.

15. A pharmaceutical composition for antagonizing the effects of substance P in a mammal, comprising a substance P antagonizing effective amount of a compound according to claim 1 and a pharmaceutically acceptable carrier.

16. A method of antagonizing the effects of substance P in a mammal, comprising administering to said mammal a substance P antagonizing effective amount of a compound according to claim 1.

17. A pharmaceutical composition for treating a condition in a mammal, the treatment of which is effected or facilitated by a decrease in substance P mediated neurotransmission, comprising an amount of a compound according to claim 1 effective in antagonizing the effect of substance P at its receptor site and a pharmaceutically acceptable carrier.

18. A method of treating a condition in a mammal, the treatment of which is effected or facilitated by a decrease in substance P mediated neurotransmission, comprising administering to a mammal in need of such treatment an amount of a compound according to claim 1, or a pharmaceutically acceptable salt thereof, effective in antagonizing the effect of substance P at its receptor site.

19. A pharmaceutical composition for treating a condition in a mammal, the treatment of which is effected or facilitated by a decrease in substance P mediated neurotransmission, comprising an amount of a compound according to claim 1, or a pharmaceutically acceptable salt thereof, effective in treating such condition and a pharmaceutically acceptable carrier.

20. A method of treating a condition in mammal, the treatment of which is effected or facilitated by a decrease in substance P mediated neurotransmission, comprising administering to a mammal in need of such treatment an amount of a compound according to claim 1 effective in treating such condition.

* * * * *